(12) United States Patent
Buchberger

(10) Patent No.: US 8,948,578 B2
(45) Date of Patent: Feb. 3, 2015

(54) INHALER COMPONENT

(71) Applicant: BATMARK Limited, London (GB)

(72) Inventor: Helmut Buchberger, Ennsdorf (AT)

(73) Assignee: BATMARK Limited, London (GB)

( * ) Notice: Subject to any disclaimer, the term of this patent is extended or adjusted under 35 U.S.C. 154(b) by 0 days.

(21) Appl. No.: 14/353,256

(22) PCT Filed: Oct. 18, 2012

(86) PCT No.: PCT/EP2012/070647
§ 371 (c)(1),
(2) Date: Apr. 21, 2014

(87) PCT Pub. No.: WO2013/057185
PCT Pub. Date: Apr. 25, 2013

(65) Prior Publication Data
US 2014/0286630 A1    Sep. 25, 2014

(30) Foreign Application Priority Data

Oct. 21, 2011    (AT) .................................. A1543/2011

(51) Int. Cl.
*F24F 6/08*    (2006.01)
*A24F 47/00*    (2006.01)
(52) U.S. Cl.
CPC ...................................... *A24F 47/00* (2013.01)
USPC ....................... 392/395; 392/386; 128/203.27
(58) Field of Classification Search
None
See application file for complete search history.

(56) References Cited

U.S. PATENT DOCUMENTS 2,809,634 A    10/1957 Murai
3,402,724 A     9/1968 Blount
(Continued)

FOREIGN PATENT DOCUMENTS

AT    507187 B1    3/2010
CH    698603 B1    9/2009
(Continued)

OTHER PUBLICATIONS

International Preliminary Report on Patentability, mailed May 1, 2014, for International Patent Application No. PCT/EP2012/070647, filed Oct. 18, 2012.
(Continued)

*Primary Examiner* — Thor Campbell
(74) *Attorney, Agent, or Firm* — N W Poulsen; L A Pinol

(57) ABSTRACT

The invention relates to an inhaler component for the formation of a vapor-air mixture and/or a condensation aerosol by evaporation of a liquid material and optionally the condensation of the formed vapor, comprising: a housing, an electric heating element for the evaporation of a portion of the liquid material; a wick with a capillary structure, said wick forming a compound structure with the heating element and automatically supplying the heating element with the liquid material; a carrier plate, preferably a printed circuit board, which carries the compound structure and on which the heating element is electrically contacted; and a capillary gap, formed at least in part by the carrier plate, for automatically supplying liquid material to the compound structure in that an end section of the wick protrudes into the capillary gap. To improve the supply of liquid material to the compound structure, it is proposed that both the front side and the rear side of the carrier plate, at least in some sections, should form the boundary walls of the capillary gap.

18 Claims, 19 Drawing Sheets

(56) References Cited

U.S. PATENT DOCUMENTS

Figure 3A:
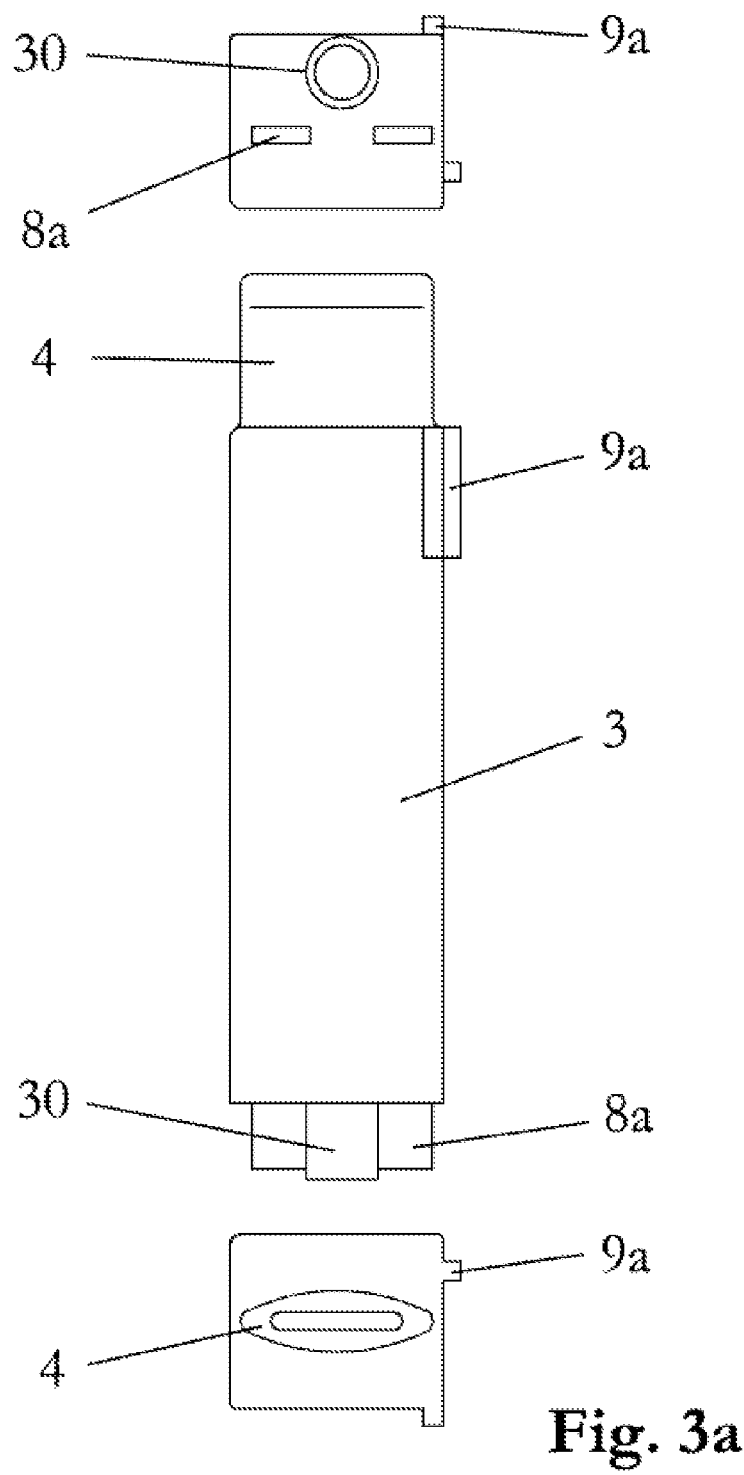

| | | |
|---|---|---|
| 3,521,643 A | 7/1970 | Toth |
| 3,804,100 A | 4/1974 | Fariello |
| 4,031,906 A | 6/1977 | Knapp |
| 4,094,119 A | 6/1978 | Sullivan |
| 4,145,001 A | 3/1979 | Weyenberg et al. |
| 4,161,283 A | 7/1979 | Hyman |
| 4,503,851 A | 3/1985 | Braunroth et al. |
| 4,588,976 A | 5/1986 | Jaselli |
| 4,735,217 A | 4/1988 | Gerth et al. |
| 4,917,301 A | 4/1990 | Munteanu |
| 4,922,901 A | 5/1990 | Brooks et al. |
| 5,060,671 A | 10/1991 | Counts et al. |
| 5,095,921 A | 3/1992 | Losee et al. |
| 5,121,881 A * | 6/1992 | Lembeck ............... 239/44 |
| 5,179,966 A | 1/1993 | Losee et al. |
| 5,247,947 A | 9/1993 | Clearman et al. |
| 5,322,075 A | 6/1994 | Deevi et al. |
| 5,501,236 A | 3/1996 | Hill et al. |
| 5,540,241 A | 7/1996 | Kim |
| 5,636,787 A | 6/1997 | Gowhari |
| 5,649,554 A | 7/1997 | Sprinkel et al. |
| 6,155,268 A * | 12/2000 | Takeuchi ............... 131/273 |
| 7,100,618 B2 | 9/2006 | Dominguez |
| 7,832,410 B2 | 11/2010 | Hon |
| 8,156,944 B2 | 4/2012 | Hon |
| 8,365,742 B2 | 2/2013 | Hon |
| 8,375,957 B2 | 2/2013 | Hon |
| 8,393,331 B2 | 3/2013 | Hon |
| 8,490,628 B2 | 7/2013 | Hon |
| 8,511,318 B2 | 8/2013 | Hon |
| 8,689,805 B2 | 4/2014 | Hon |
| 8,752,545 B2 | 6/2014 | Buchberger |
| 2003/0049025 A1 | 3/2003 | Neumann et al. |
| 2004/0129793 A1 | 7/2004 | Nguyen et al. |
| 2005/0268911 A1 | 12/2005 | Cross et al. |
| 2007/0102013 A1 | 5/2007 | Adams et al. |
| 2007/0155255 A1 | 7/2007 | Galauner et al. |
| 2009/0188490 A1 | 7/2009 | Han |
| 2011/0226236 A1 * | 9/2011 | Buchberger ............ 128/200.23 |
| 2011/0290267 A1 | 12/2011 | Yamada et al. |
| 2011/0297166 A1 | 12/2011 | Takeuchi et al. |
| 2013/0074857 A1 | 3/2013 | Buchberger |
| 2013/0081623 A1 | 4/2013 | Buchberger |
| 2013/0333700 A1 | 12/2013 | Buchberger |
| 2014/0202454 A1 | 7/2014 | Buchberger |
| 2014/0238396 A1 | 8/2014 | Buchberger |

FOREIGN PATENT DOCUMENTS

| | | |
|---|---|---|
| EP | 2340729 A1 | 7/2011 |
| WO | 03/028409 A1 | 4/2003 |
| WO | 2010/045670 A1 | 4/2010 |
| WO | 2010/045671 A1 | 4/2010 |

OTHER PUBLICATIONS

International Search Report and Written Opinion, mailed Feb. 6, 2013 for PCT/EP2012/070647, filed Oct. 18, 2012.

* cited by examiner

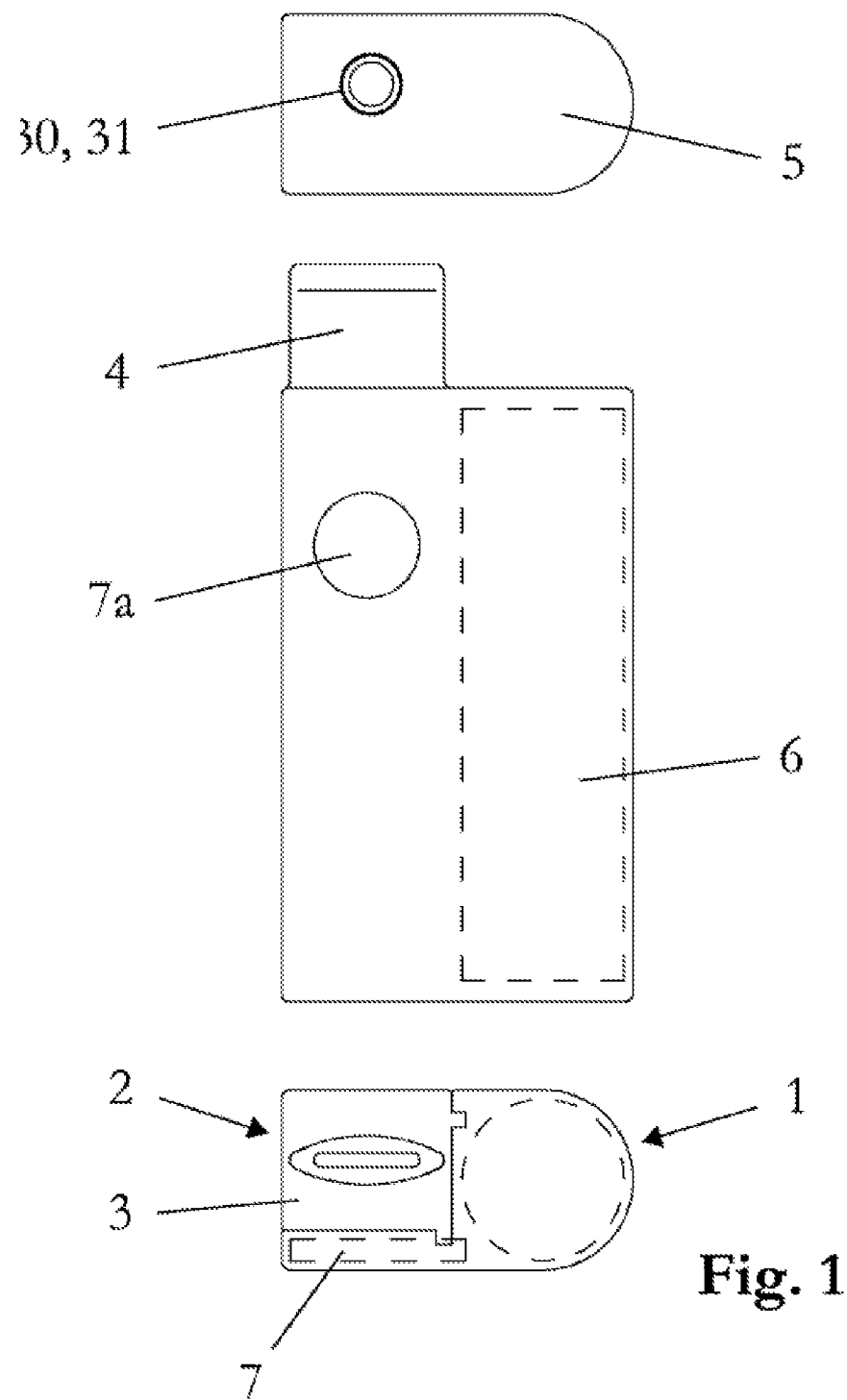

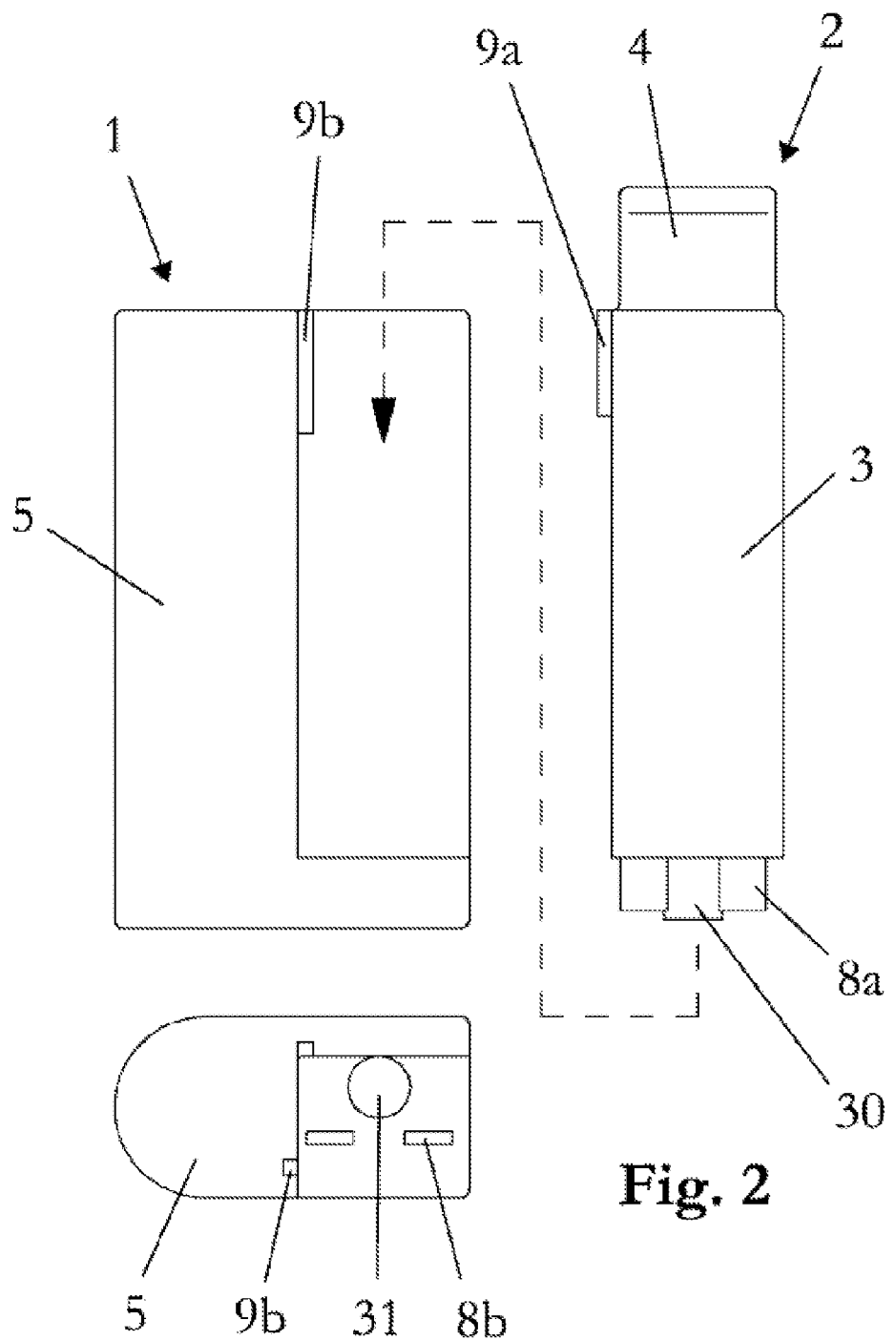

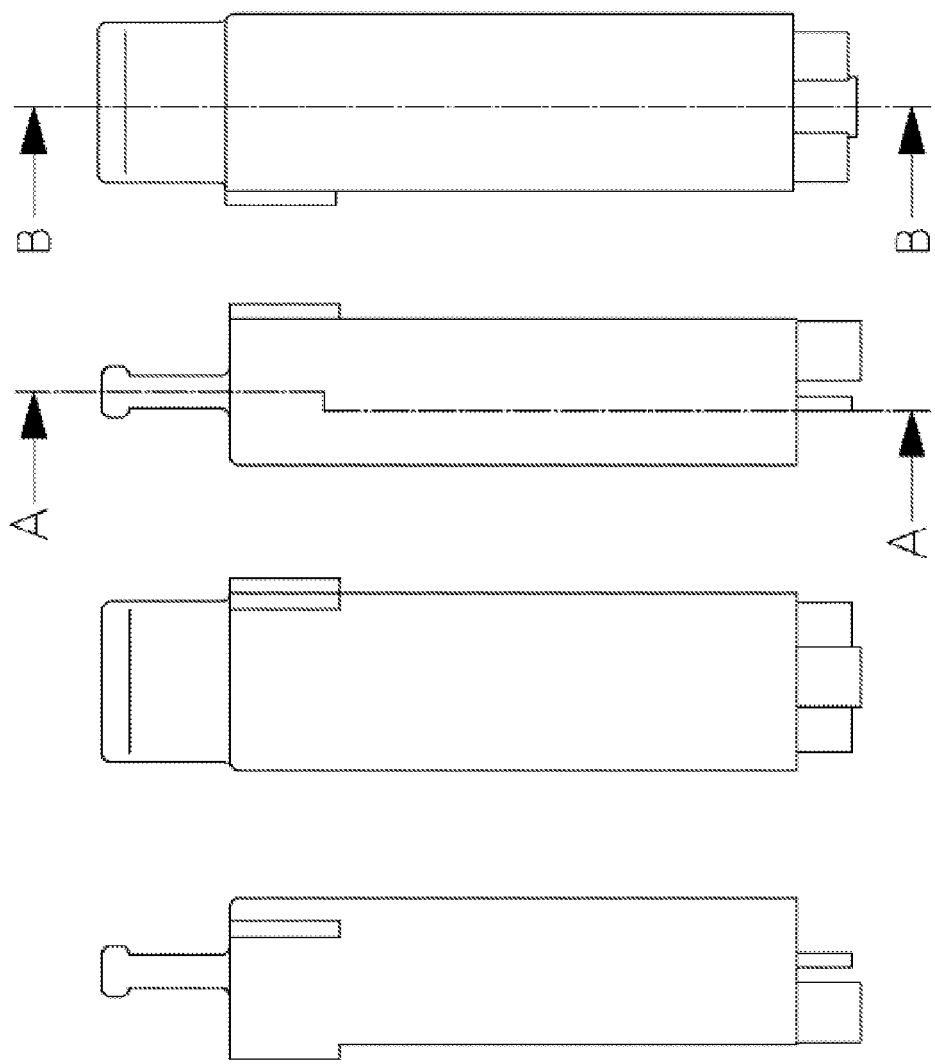

US 8,948,578 B2

INHALER COMPONENT

CLAIM FOR PRIORITY

This application is the National Stage of International Application No. PCT/EP2012/070647, filed Oct. 18, 2012, which in turn claims priority to and benefit of Austrian Patent Application No. AT A1543/2011, filed Oct. 21, 2011. The entire contents of the aforementioned applications are herein expressly incorporated by reference.

The invention concerns an inhaler component for the formation of a vapor and air mixture and/or a condensation aerosol by evaporation of a liquid material and optionally by condensation of the resulting vapor, comprising:
    a housing;
    an electrical heating element to evaporate a portion of the liquid material;
    a wick with a capillary structure, which wick forms a compound structure with the heating element and automatically supplies the heating element with the liquid material;
    a carrier plate, preferably a circuit board, which carries the compound structure and on which the heating element makes electrical contact;
    a capillary gap at least partly formed by the carrier plate for the automatic supplying of the compound structure with the liquid material in that an end segment of the wick protrudes into the capillary gap.

DEFINITION OF TERMS

In the present patent application, the term "inhaler" refers to medical as well as nonmedical inhalers. Moreover, the term refers to inhalers for administering of pharmaceuticals and substances that have not been declared to be pharmaceuticals. The term furthermore refers to smoking articles and cigarette replacement articles, such as are contained in the European patent class A24F47/00B, insofar as these are designed to provide the user with a mixture of vapor and air, and/or a condensation aerosol. The term "inhaler" should also make no limitations as to how the resulting mixture of vapor and air and/or condensation aerosol is supplied to the user or his body. The mixture of vapor and air and/or condensation aerosol can be inhaled into the lungs, or also only be taken to the oral cavity—without inhalation into the lungs.

A "capillary gap" is considered to be any gap that brings about a liquid transport simply by virtue of the capillary action of its bounding walls. Wicks, jacketed wicks, or channels filled with wick material are not capillary gaps.

The use of the singular "compound structure" does not preclude the presence of several compound structures. The invention explicitly includes arrangements with several compound structures.

WO 2010/045671 (Helmut Buchberger) specifies an inhaler component for the intermittent, inhalation or draw-synchronized formation of a mixture of vapor and air and/or condensation aerosol, consisting of (FIG. 9-12 and FIG. 17-18) a housing 3, a chamber 21 arranged in the housing 3, an air inlet opening 26 for the supply of air from the surroundings into the chamber 21, an electrical heating element for evaporating a portion of a liquid material 16, whereupon the resulting vapor mixes in the chamber 21 with the air supplied by the air inlet opening 26, and the mixture of vapor and air and/or condensation aerosol is formed. The inhaler component furthermore comprises a wick with a capillary structure, which wick forms a sheetlike compound structure 22 with the heating element and automatically supplies the heating element with the liquid material 16 once again after an evaporation. The sheetlike compound structure 22 is mounted by two end segments on two electrically conducting platelike contacts 23, on whose surface the heating element at the same time makes electrical contact. The platelike contacts 23 can also be formed alternatively by circuit boards or one shared circuit board. At least one heated segment of the sheetlike compound structure 22 is arranged free of contact in the chamber 21, and the capillary structure of the wick lies in said segment for the most part free, at least on one side 24 of the sheetlike compound structure. The sheetlike compound structure 22 or its wick protrudes by one end into a capillary gap 41, which for its part is capillary coupled or can be coupled to a liquid container 4 containing the liquid material 16. The liquid container 4 has a closure 18 that can be opened, which is still closed prior to use. The closure 18 can be manually opened by the user, whereupon the liquid material 16 floods a reservoir 45 and wets the capillary gap 41. The capillary gap 41 draws the liquid material 16 from the liquid container 4 or reservoir 45 and transports it to the compound structure 22. The capillary gap 41 is formed basically by one of the two platelike contacts 23 and a top piece 42 placed on the surface of the latter, in that the two adjoining structural elements or their surfaces form boundary walls of the capillary gap 42. Furthermore, a ventilation channel 52 is worked into the platelike contact 23, which connects the reservoir 45 or the liquid container 4 to the chamber 21. The ventilation channel 52 produces a pressure equalization in that each portion of liquid material 16 arriving in the capillary gap 41 is immediately replaced by an equal-volume portion of air.

Figure 11:
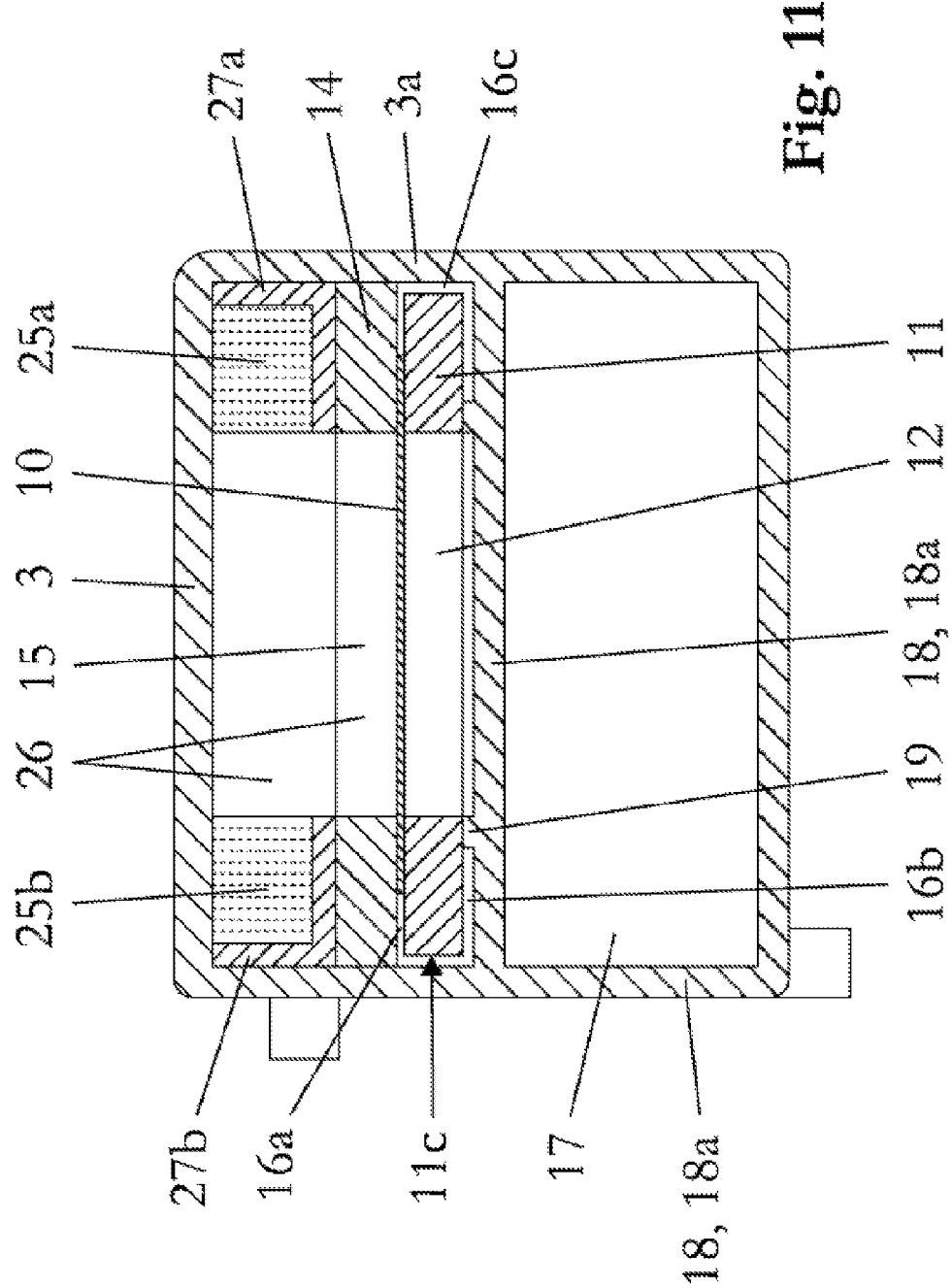

Finally, a storage buffer 53 is integrated in the top piece 42, which communicates with the capillary gap 41 and itself consists of capillaries—see FIG. 11 and FIG. 17. The storage buffer 53 has the ability to take up liquid material 16 from the capillary gap 41, store it temporarily, and return it to the capillary gap 41 when needed. In this way, the inhaler component can also be operated in an inverted position—the mouth piece 5 pointing downward—at least for as long as liquid material 16 is on hand in the storage buffer 53. The storage buffer 53 consists of parallel arranged slits 54 that are worked into the top piece 42. The slits 54 communicate, on the one hand, via openings 55 with the capillary gap 41 and on the other hand via a ventilation gap 56 with the chamber 21. The capillarity of the slits 54 has the effect that the liquid material 16 flows from the reservoir 45 via the capillary gap 41 and via the openings 55 into the slits 54, where it is temporarily stored, and it can be pulled back again by the capillary gap 41 as needed.

The design of the storage buffer 53 proves to be extremely bulky. The fabrication of the fine slits 54 and openings 55 worked into the top piece 42 is also relatively costly. Finally, it is a disadvantage that the openings 55 disturb the capillarity of the capillary gap 41, because otherwise wettable wall segments of the capillary gap 41 are lost by the openings 55. In the worst case, the disturbance of the capillarity can impair the supply of the sheetlike compound structure 22 with the liquid material 16.

The problem on which the invention is based is to eliminate the aforementioned drawbacks of the arrangement known from the prior art. In particular, the invention is based on the problem of configuring an inhaler component of the kind described above by simple design features so that sufficient quantities of liquid material can be buffered without requiring a substantial additional construction space. Furthermore, the reliability of supplying the compound structure with the liquid material should be enhanced.

The problem is solved by the characterizing features of patent claim 1. Accordingly, it is specified that both the front side and the back side of the carrier plate form boundary walls of the capillary gap, at least for a portion. Thus, the supplying of the compound structure with the liquid material occurs not merely on one side of the carrier plate, but on both sides. On both sides of the carrier plate there are provided capillary gaps or capillary gap segments that are bounded by the carrier plate. In this way, an additional capillary gap volume can be created in a simple and space-saving manner, serving at the same time as a buffer. Another beneficial effect is to be seen in the redundancy of the liquid supply: if the supply fails in one capillary gap segment—for whatever reason—the compound structure can still be supplied with the liquid material at least via the capillary gap segment lying on the other side of the carrier plate.

In a modification of the invention, it is specified that the edge of the carrier plate also forms at least a portion of a boundary wall of the capillary gap. In this way, the buffer volume can be further increased. It is especially beneficial for the capillary gap to at least partly encloses the carrier plate. The enclosure has the effect that the capillary gap segments at the front and back side of the carrier plate communicate with each other via the edge of the carrier plate. Even if the capillary liquid flow were to be interrupted at several places of the capillary gap, there would be at least one alternative pathway to go around the affected places.

According to the invention, over 50 percent of the carrier plate surface form boundary walls of the capillary gap. Segments of the carrier plate sticking out from the housing are not counted in the calculation. Thanks to the large-scale usage of the carrier plate surface as a boundary wall for the capillary gap, the aforementioned effects as to the formation of an additional buffer volume and the enhancing of the supply reliability are maximized. Moreover, the supply capacity, which is the maximum delivered quantity of liquid material through the capillary gap per unit of time, can be increased.

It is especially advantageous when the capillary gap is formed at least partially by the carrier plate and an adjoining wall of the housing. In this case, the capillary gap is formed, at least partly, solely by components already available. Already present wall segments of the housing are used as boundary walls of the capillary gap. No additional construction space is required.

One preferred embodiment of the invention concerns an inhaler component with a liquid container containing the liquid material from which the capillary gap draws the liquid material, and it is specified that the capillary gap is at least partially formed by the carrier plate and an adjacent wall of the liquid container. The liquid container can either form an independent structural part, or be part of the housing. In the latter case, the liquid container is formed by walls of the housing. Especially favorable conditions result when the capillary gap communicates via a supply opening in the wall of the liquid container with the liquid material in the liquid container, in that the wall of the liquid container forms a shoulder at the edge of the supply opening and the carrier plate abuts against the shoulder with its edge. Accordingly, no additional means are needed to connect the capillary gap to the liquid container. Thanks to the shoulder, a wall segment of the supply opening is extended outwardly. If one assumes that the surfaces involved are readily wettable by the liquid material, the result is that a small quantity of liquid material is drawn out from the supply opening by the forces of adhesion acting at the lengthened wall segment. The effect is sufficient for the liquid material to also reach and wet the carrier plate abutting by its edge against the shoulder. Thus, the capillary gap is coupled to the liquid material in the liquid container and can become filled with the liquid material, driven by the capillary forces acting in it.

The invention furthermore involves an inhaler, comprising an inhaler component according to the invention as described above. The inhaler component can thus also be only a part, especially an interchangeable part, of an inhaler.

Figure 4A:
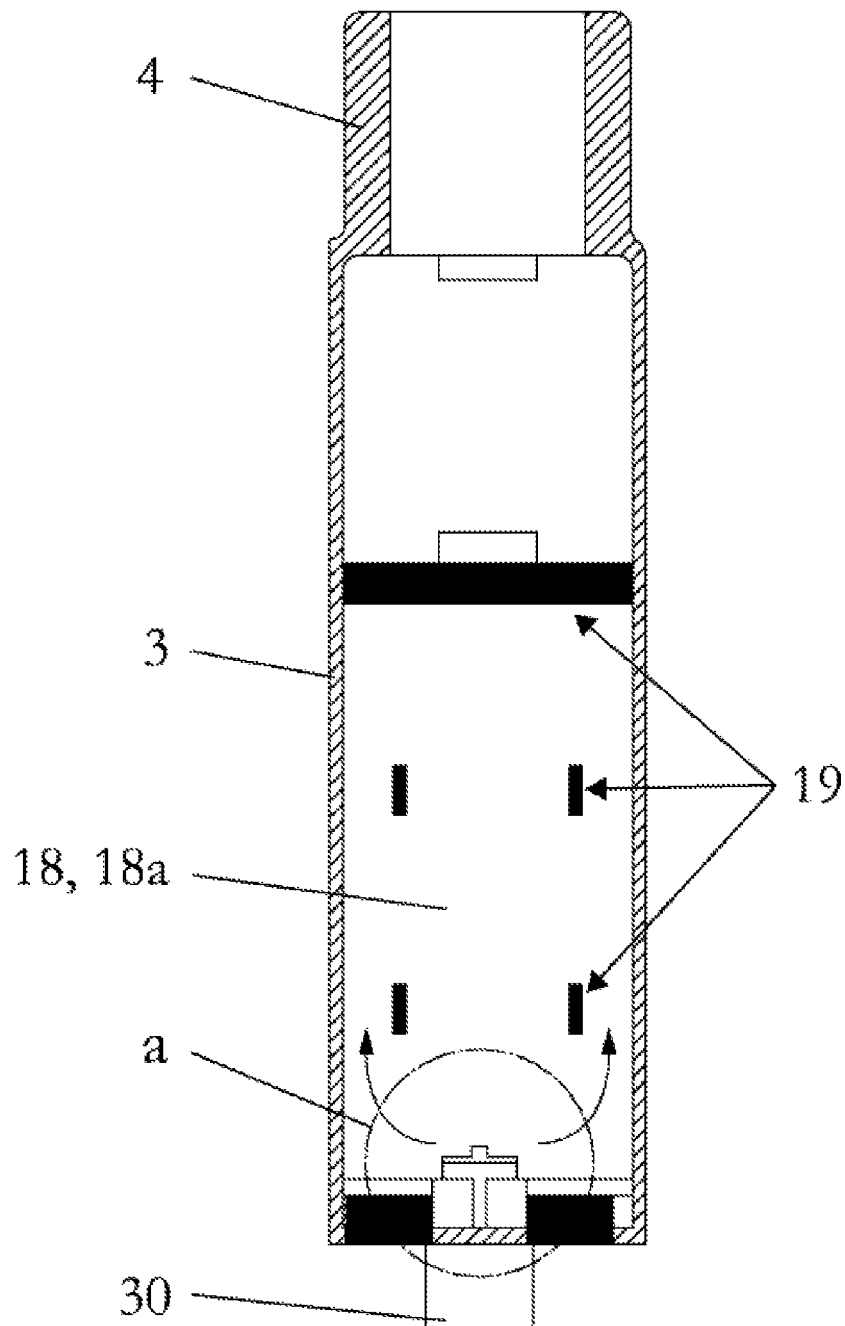
Figure 4B:
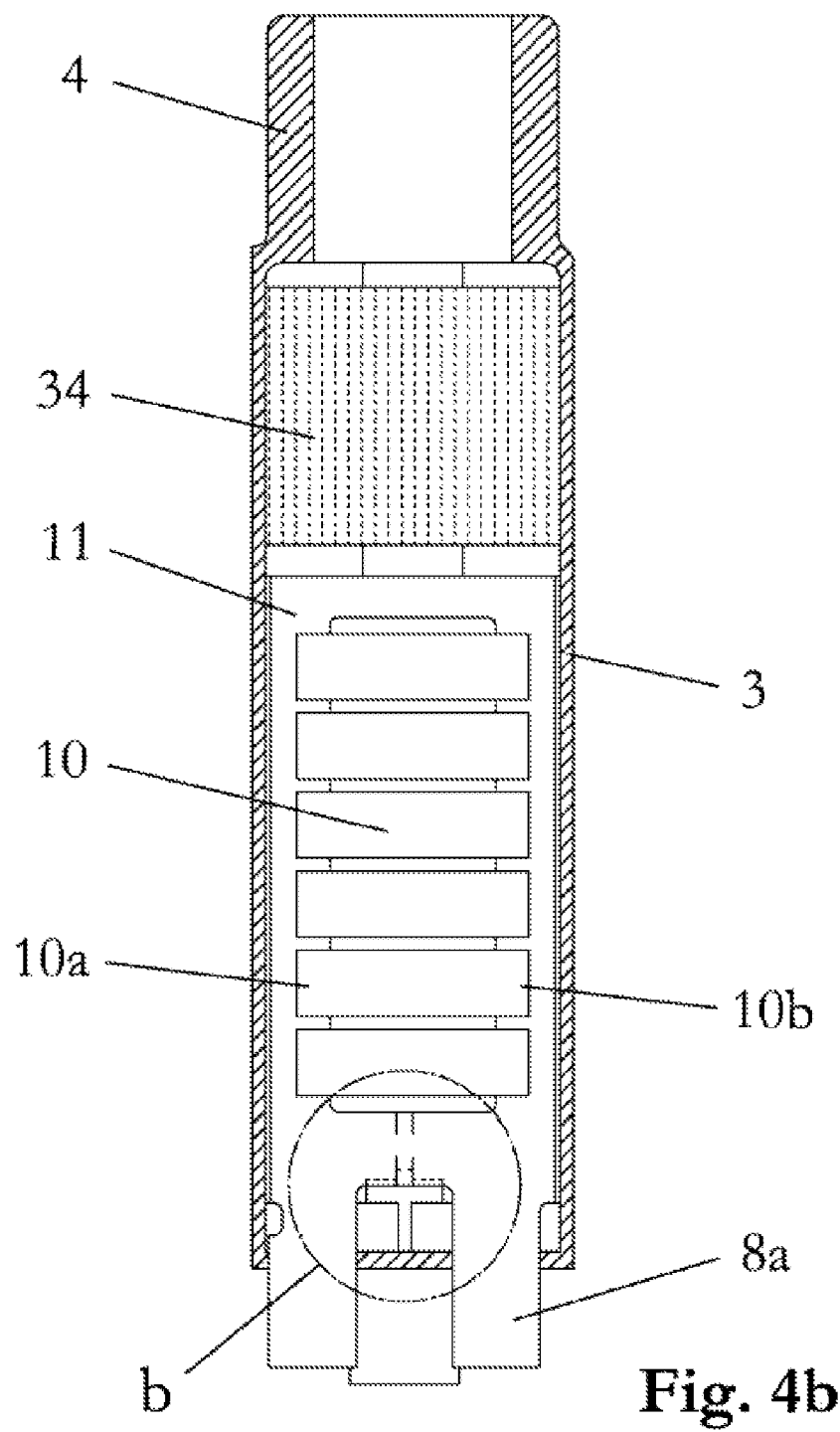
Figure 5:
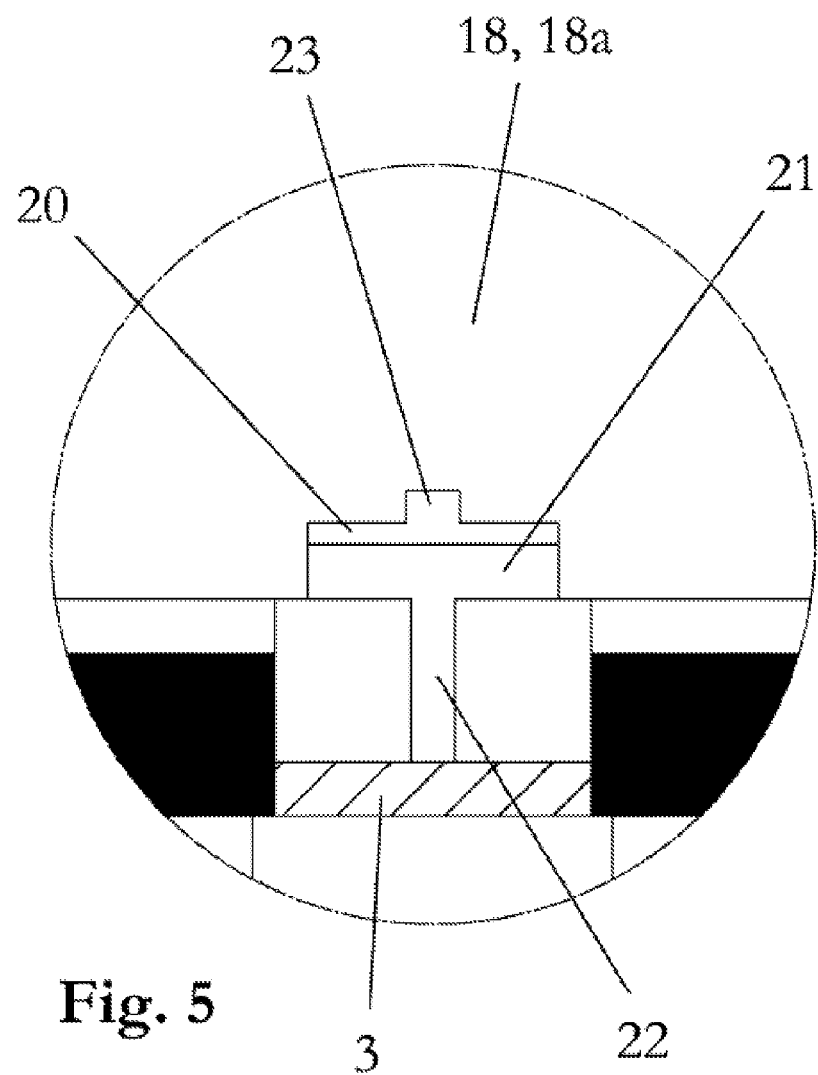
Figure 6:
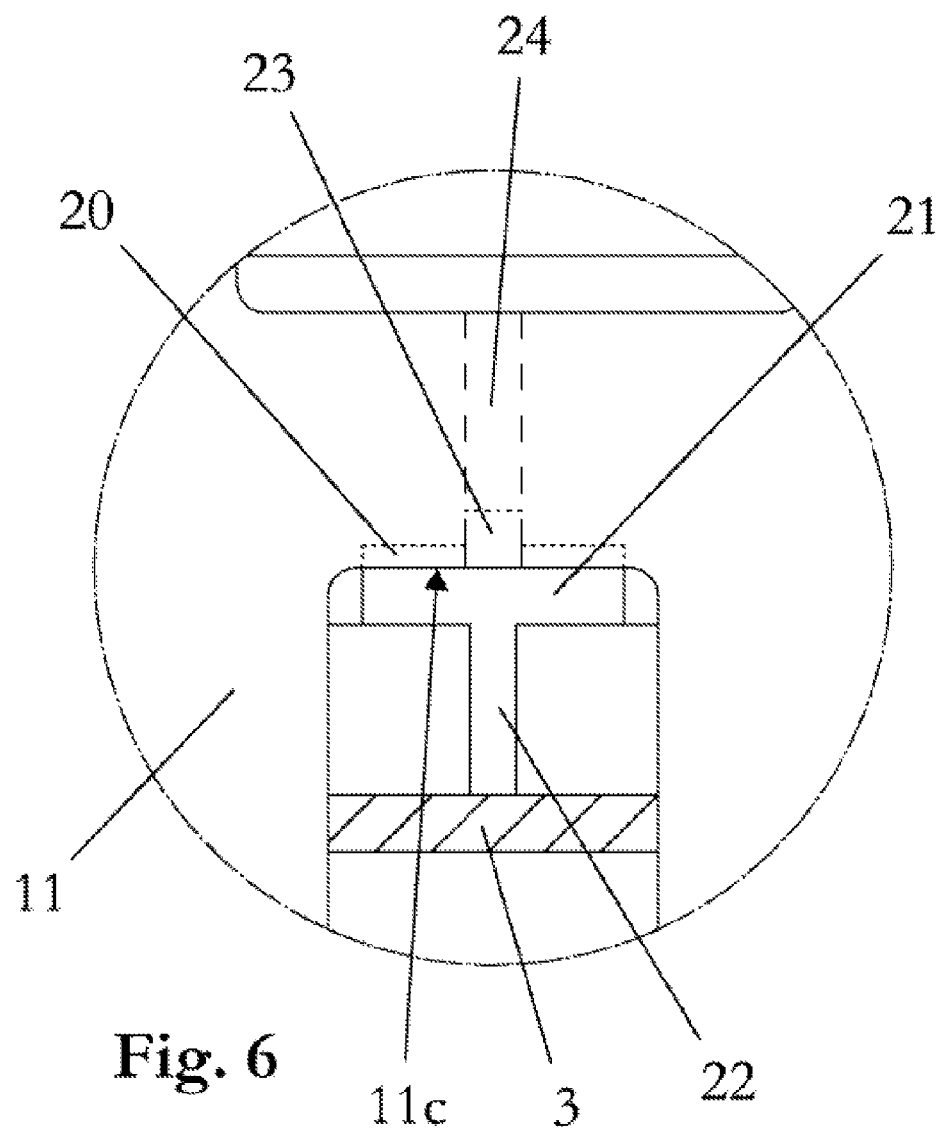
Figure 7:
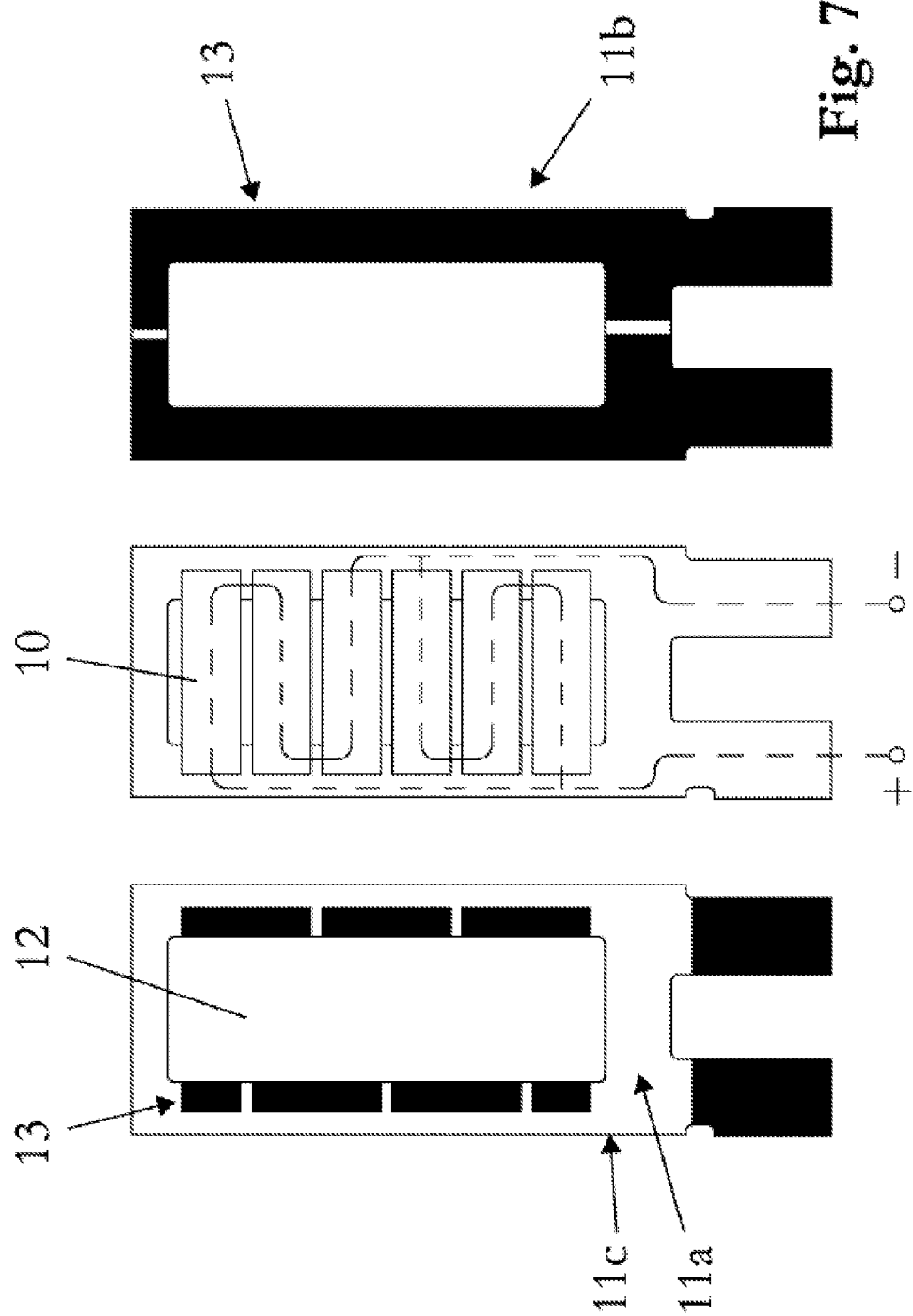
Figure 8:
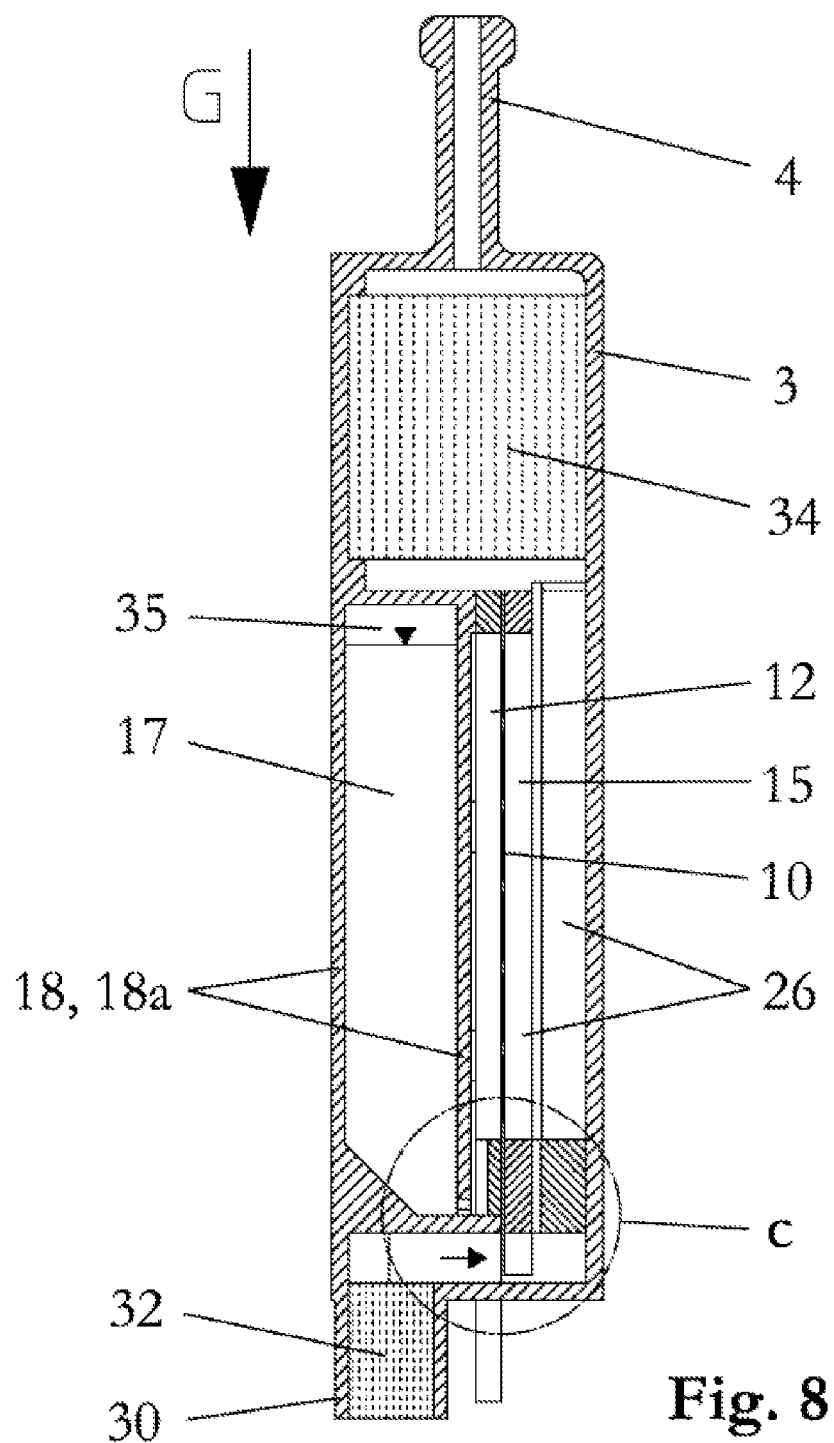
Figure 9:
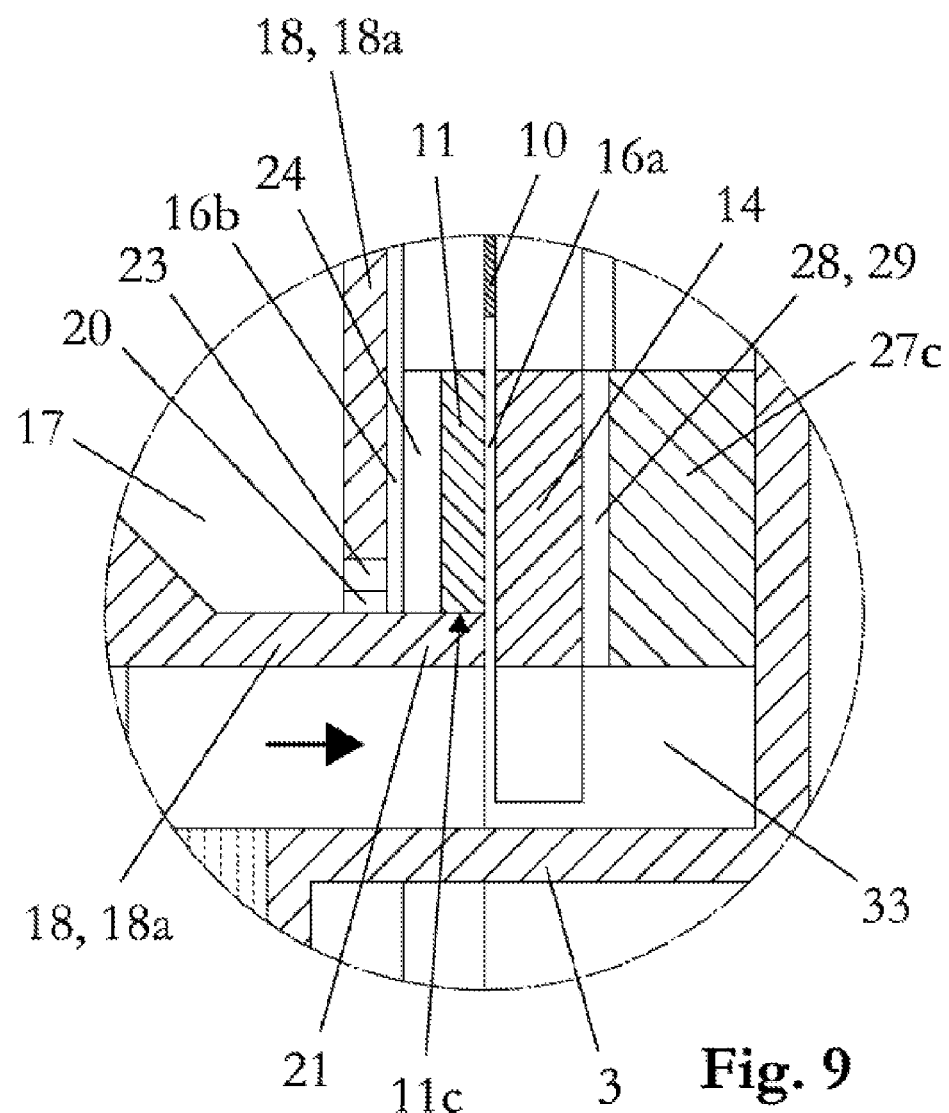
Figure 10:
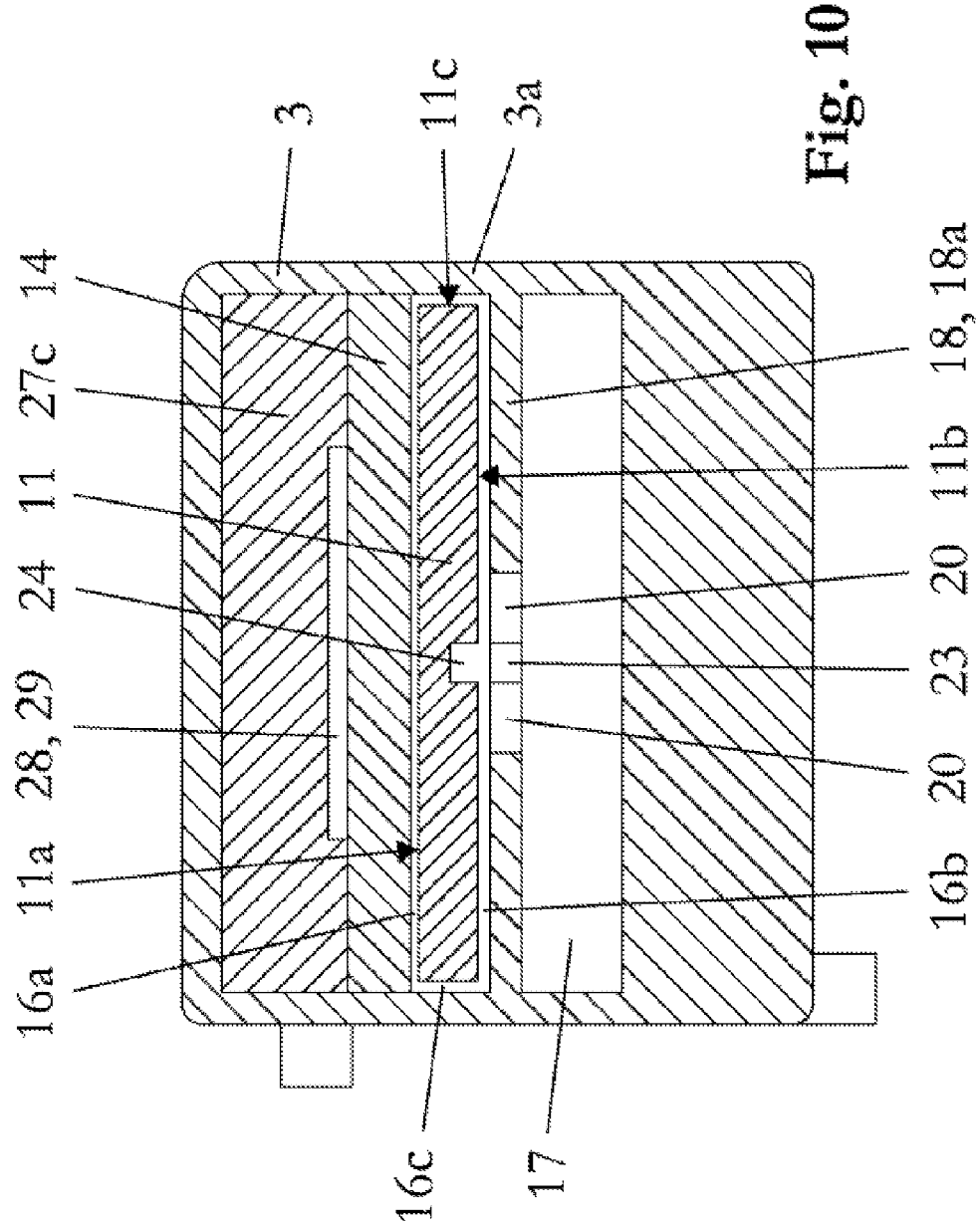

The invention will now be explained more closely by means of a sample embodiment according to the drawings. There are shown:

FIG. 1, an inhaler according to the invention in various views;

FIG. 2, the inhaler of FIG. 1 with a reusable inhaler part and an interchangeable inhaler component in the decoupled state;

FIG. 3a and FIG. 3b, the interchangeable inhaler component in various views;

FIG. 4a, FIG. 4b, FIG. 4c, FIG. 4d, FIG. 4e, FIG. 4f, FIG. 4g, sectional views of the interchangeable inhaler component along line A-A in FIG. 3b in various assembly states;

FIG. 5, detail a of FIG. 4a in a magnified view;

FIG. 6, detail b of FIG. 4b in a magnified view;

FIG. 7, a carrier plate configured as a multilayer circuit board;

FIG. 8, a sectional view of the interchangeable inhaler component along line B-B in FIG. 3b;

FIG. 9, detail c of FIG. 8 in a magnified view;

FIG. 10, a cross section of the interchangeable inhaler component at the level of the supply opening;

FIG. 11, a cross section of the interchangeable inhaler component at the level of the compound structures.

Figure 12:
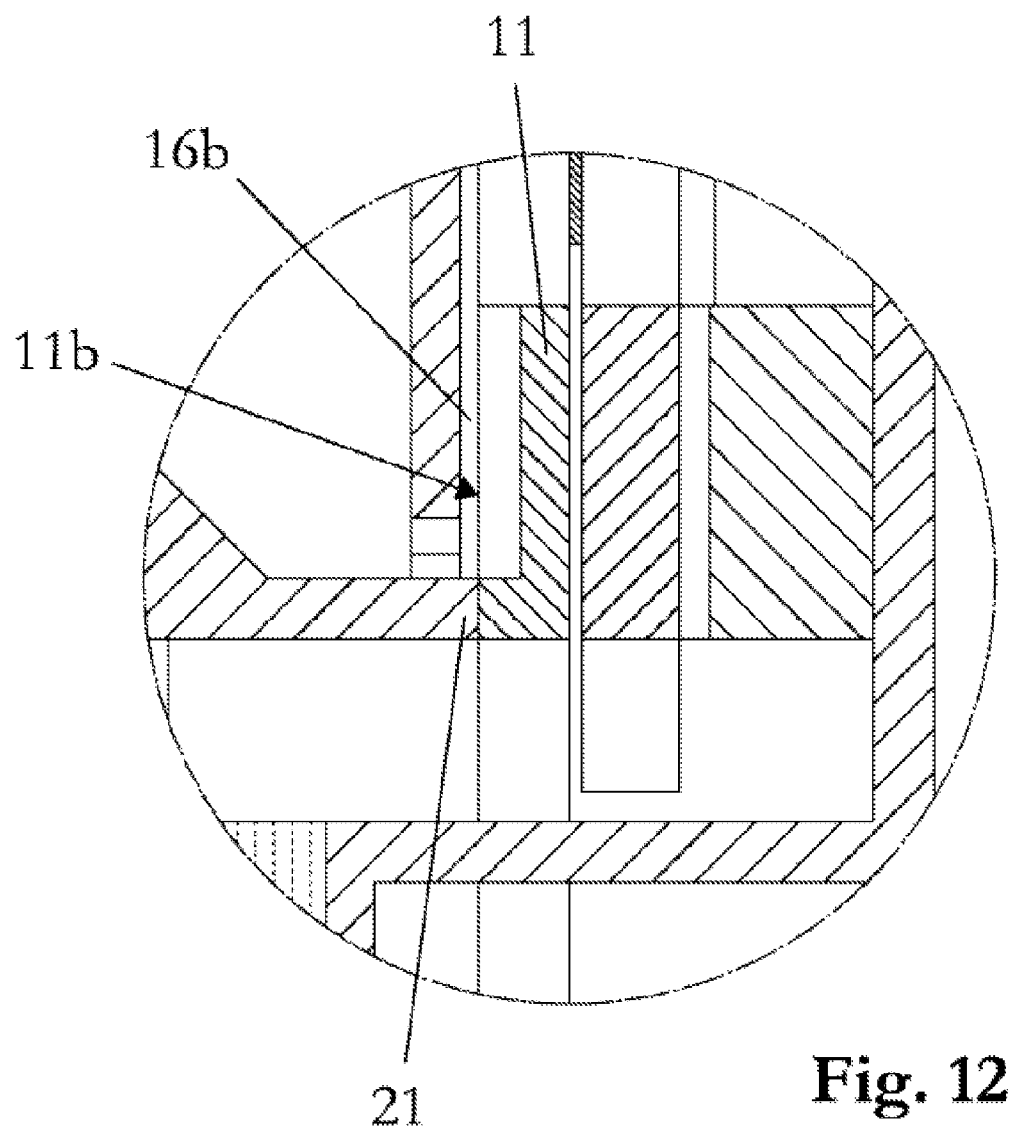

FIG. 12, an alternative configuration of detail c (see FIG. 9).

FIG. 1 shows an inhaler according to the invention, whose form and size are configured so that the inhaler can be easily and conveniently handled by the user. In terms of volume, the inhaler is only around half the size of a cigarette pack. The sample inhaler depicted consists essentially of two parts, namely, an inhaler part 1 and an inhaler component 2.

The inhaler component 2 consists of a housing 3, which forms a tobacco pipe-like mouthpiece 4 at one end face. The inhaler component 2 contains a liquid material, which is electrically evaporated inside the housing 3 and converted into an inhalable mixture of vapor and air and/or condensation aerosol. The resulting mixture of vapor and air and/or condensation aerosol is presented to the user via the mouthpiece 4. The liquid material can be any substance or preparation that evaporates largely free of residue under atmospheric conditions. This condition is already fulfilled when the particular substance or preparation is present in the diluted state, e.g., dissolved in water and/or ethanol, and the solution evaporates largely free of residue. Thanks to a sufficiently good dilution in an easily volatile solvent such as water and/or ethanol, even otherwise hard to evaporate substances can meet the above-given condition, and a thermal decomposition of the liquid material is avoided or substantially reduced.

The aerosol particles produced by condensation generally have a mass median aerodynamic diameter (MMAD) less than 2 μm and therefore also reach the alveoli. The inhaler of the invention is especially suitable for the administering of substances with systemic action—especially those active substances that deploy their main action in the central nervous system. As an example, one can mention nicotine, whose boiling point is 246° C. The nicotine-containing aerosol particles are deposited primarily in the bronchi and alveoli, where the active substance passes into the blood stream lightning-fast. A few seconds later the nicotine reaches the brain in concentrated form and can deploy the known effects there.

The inhaler part 1 consists of a main housing 5, which again is preferably made of plastic. The main housing 5 contains at least one battery 6 and an electrical circuit 7 (shown by broken line in FIG. 1) with switch 7a. The battery 6 and the electrical circuit 7 provide the electrical energy needed for the evaporation of the liquid material. The battery 6 consists preferably of a rechargeable battery, such as the type CGR18650K from Panasonic, www.industrial.panasonic.com. This is a cylindrical lithium ion cell of size 18650 with a storage capacity of 1650 mAh and a current load capacity up to 30 A. Comparable cells are also manufactured by other manufacturers, such as Sony, Samsung, LG Chem, in large numbers.

As is shown by FIG. 2, the inhaler part 1 and the inhaler component 2 in the specific sample embodiment are detachable from each other. This arrangement makes the inhaler part 1 reusable, which is basically sensible if one considers that, first, the inhaler part 1 does not come into contact with the liquid material, i.e., it is not contaminated with the liquid material, and secondly it contains components that are more long-lived than the components of the inhaler component 2. The inhaler component 2, after the liquid material is used up, is properly disposed of as a whole by the user, and replaced by a new inhaler component 2. In this respect, the inhaler component 2 constitutes an interchangeable, disposable article. A proper disposal is especially appropriate when the liquid material contains pharmaceuticals or poisons such as nicotine. Basically, of course, it would also be conceivable to make the inhaler part 1 and the inhaler component 2 as a single piece, i.e., not detachable from each other. However, this configuration would be less economical, because in this case all parts and components of the inhaler, i.e., the inhaler as a whole, would form a disposable article for onetime use. Of course, the present invention also includes this embodiment, but in this case the entire inhaler is to be understood as being the inhaler component.

The mechanical coupling between the interchangeable inhaler component 2 and the reusable inhaler part 1 occurs by insert tongues 8a and guide lugs 9a formed by the housing 3, which fit into corresponding insert sockets 8b and guide grooves 9b formed by the main housing 5 of the reusable inhaler part 1. The insert tongues 8a and insert sockets 8b serve at the same time to channel the electrical energy into the interchangeable inhaler component 2 for evaporation of the liquid material, as will be shown in further detail below.

FIG. 3a and FIG. 3b show different views of the interchangeable inhaler component 2. FIGS. 4-11 provide further insight into the internal construction of the inhaler component 2. Accordingly, the housing 3 of the inhaler component 2 has essentially a rectangular shape. Inside the rectangular housing 3 are the components important to the forming of a mixture of vapor and air and/or condensation aerosol. These include in particular the compound structures 10, which bring about the evaporation of the liquid material. In the specific sample embodiment, six compound structures 10 are arranged alongside each other, and the compound structures have a sheetlike shape. The sheetlike compound structures 10 each consist of a wick and an electrical heating element, which are joined together in sheet fashion or integrated with each other in sheet fashion. The sheetlike compound structures 10 can be formed, for example, by a metal foil with metal cloth layers sintered on it. Instead of the metal cloth, open-pore metal foams can also be used. The open-pore capillary structure of the cloth layers sintered on the metal foil or the metal foam form the wick, and the electrical resistance of the metal forms the heating element. Suitable metallic resistance materials are, for example, refined steels such as AISI 304 or AISI 316, as well as heat conducting alloys, especially NiCr alloys. The manufacture of such sheetlike compound structures 10 is prior art and disclosed in detail, for example in the already cited WO 2010/045671 (Helmut Buchberger). It should be noted that the sheetlike compound structures 10 need not have a flat configuration, but can also have a three-dimensional curvature.

As is best shown by FIG. 4b and FIG. 7, the sheetlike compound structures 10 are mounted by two end segments 10a, 10b on a carrier plate 11. The carrier plate 11 has a large cavity 12, across which the compound structures 10 stretch without contact. The carrier plate 11 in the specific sample embodiment is configured as a circuit board, especially a multilayer circuit board. Basically all known circuit board materials are suited as the material for the circuit board 11, especially materials of type FR1 to FR5. The sheetlike compound structures 10 are in electrical contact in the region of the end segments 10a, 10b on conductor tracks 13 of the circuit board 11. In FIG. 7, the conductor tracks 13 are shown as black areas. In the case of the aforementioned metal foil compound structures, the electrical contacting occurs preferably by a soldering at the foil side, possibly after prior treatment with a suitable flux agent. Refined steels of material grades AISI 304 and AISI 316 can be easily soldered, for example, with a solder concentrate commercially known as "5050S-Nirosta" from Stannol GmbH, www.stannol.de. Alternatively, the electrical contacting can consist of a glue connection by means of an electrically conductive adhesive, such as a silver-containing glue on an epoxy basis. The fitting of the circuit board 11 with the sheetlike compound structures 10 and the production of their contacts is done fully automatic, in which methods of the circuit board industry can be used, which methods moreover are also suited to a mass production.

The circuit board 11 protrudes from the housing 3 in the form of the already mentioned insert tongues 8a. The two insert tongues 8a serve to channel the electrical energy into the inhaler component 2. The electrical energy is supplied to the compound structures 10 via the conductor tracks 13. According to FIG. 7, the conductor tracks 13 are arranged on both the front side 11a and the back side 11b of the circuit board 11, while the front side 11a is the component mounting side, that is, the side on which the compound structures 10 make contact. Additional conductor tracks can also be arranged optionally in intermediate layers. The individual conductor track layers are advisedly joined together by means of so-called throughplatings of the prior art. FIG. 7, moreover, shows the current flow. Accordingly, in the specific example, every three compound structures 10 are hooked up in series with each other. In this way, the resulting heating resistance and thus the heating power and rate of evaporation can be influenced in certain limits. It can also be provided that the individual electrical resistances of the six compound structures 10 are of different size, for example, by appropriately varying the thickness of the metal foil. With this measure, the evaporation process can be made to depend on the location, as with a cigarette.

Figure 4C:
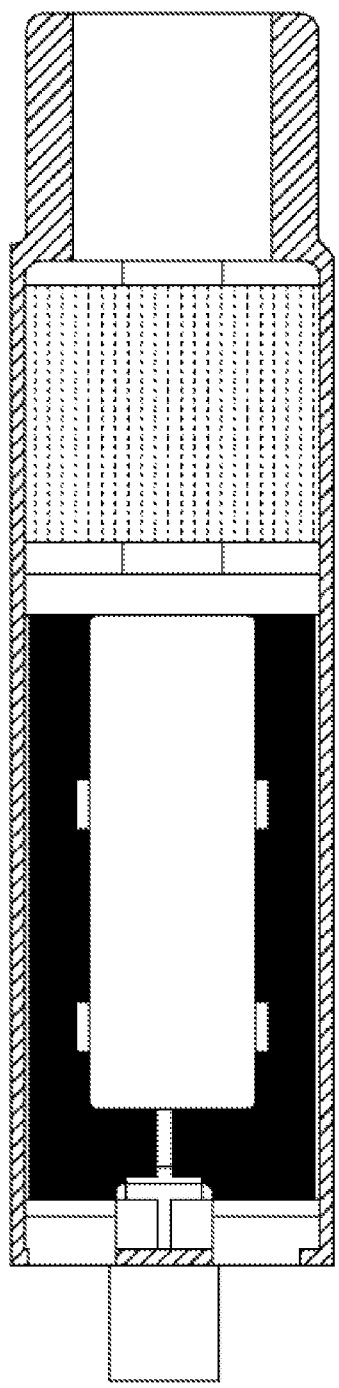
Figure 4D:
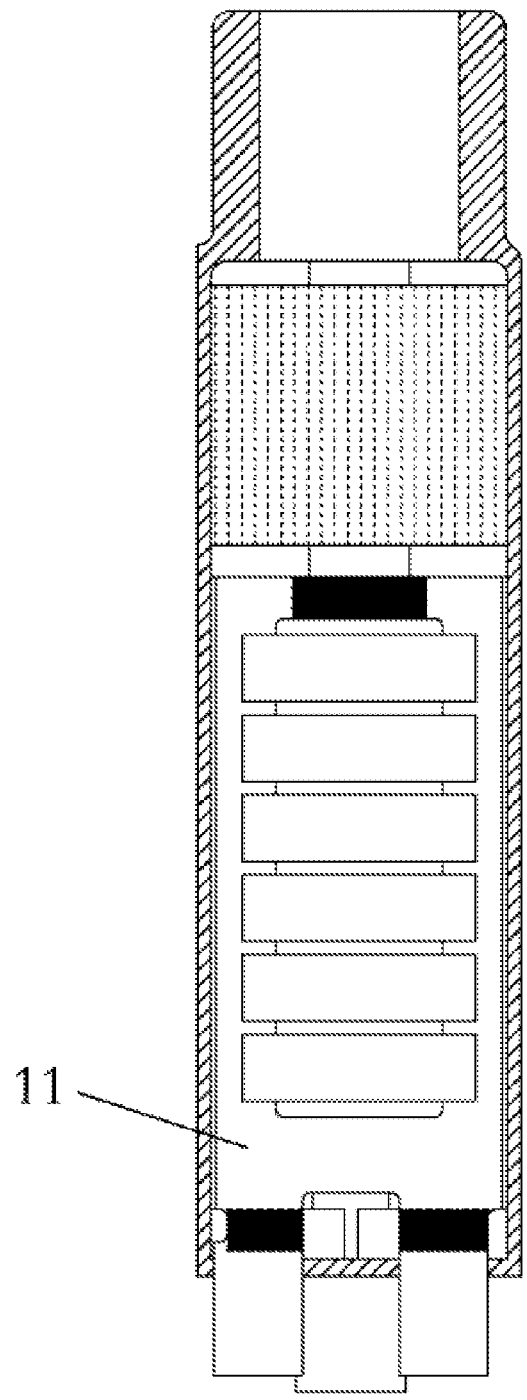
Figure 4E:
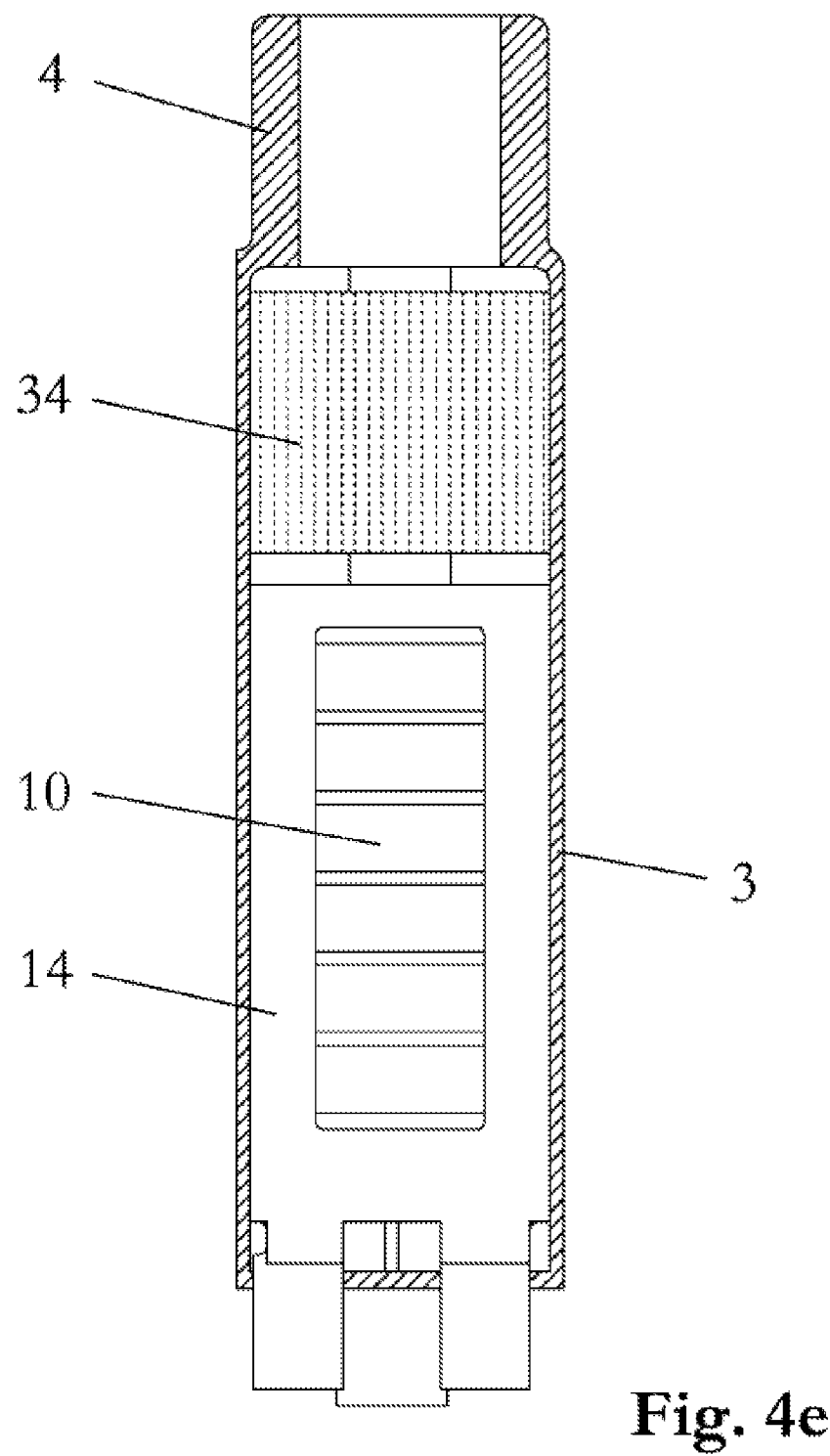
Figure 4F:
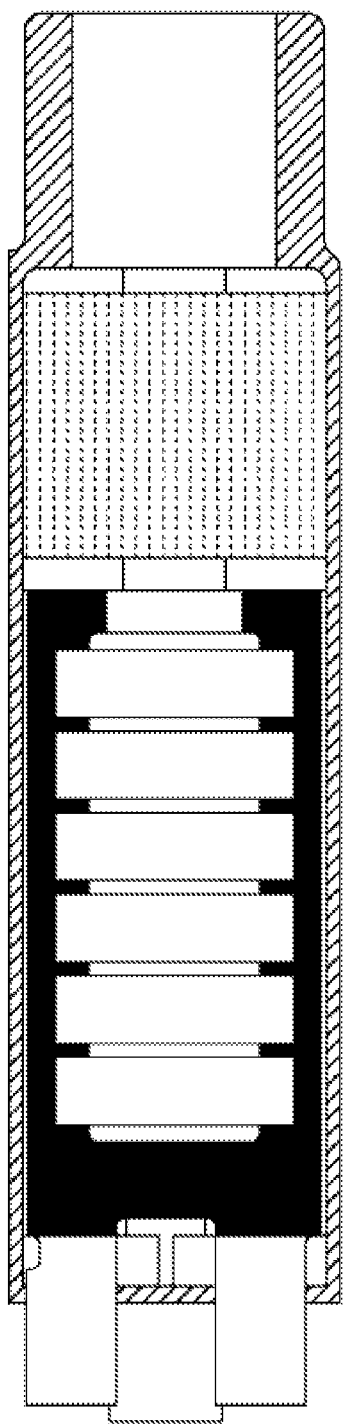

On the front side 11a of the circuit board 11 is placed an essentially platelike top piece 14, preferably made of plastic (see FIG. 4c and FIG. 8-10). The top piece 14 has a recess 15, which correlates in size and arrangement with the cavity 12 in the circuit board 11. In the most simple case, the top piece 14 is mounted directly on the end segments 10a, 10b of the sheetlike compound structures 10. In this way, the top piece 14 together with the circuit board 11 forms a first capillary gap segment 16a, whose clear width or gap width basically corresponds to the thickness of the sheetlike compound structures 10 (see FIG. 9 and FIG. 11). The gap width is typically 0.2 mm. In FIG. 4f, the two-dimensional extent of the first capillary gap segment 16a is shown as a black area. The top piece 14 is fastened to the circuit board 11 by a glue connection. The glue sites are shown as black areas in FIG. 4d. The circuit board 11 and the top piece 14 are preferably joined outside of the housing 3, i.e., they constitute a preassembled unit.

The circuit board 11 is mounted by its back side 11b at least partially on a rectangular liquid container 18 containing the liquid material 17 (see FIG. 4a/4b, FIG. 8-9 and FIG. 11). The liquid container 18 or its walls 18a are formed by the housing 3. The circuit board 11, however, is not mounted directly on the liquid container wall 18a, but rather on spacers 19. The spacers 19 are formed partly by the liquid container wall 18a and partly by other housing segments; they are shown in FIG. 4a as black areas. In this way, a second capillary gap segment 16b is formed. The back side 11b of the circuit board 11 and the adjacent liquid container wall 18a form the boundary walls of this second capillary gap segment 16b. In FIG. 4c the two-dimensional extent of the second capillary gap segment 16b is shown as a black area. The gap width is determined by the height of the spacers 19 and typically amounts to 0.3 mm. The circuit board 11 is fastened preferably by means of a glue connection to the spacers 19. The filling of the liquid container 18 with the liquid material 17 is done at the factory at the end of the manufacturing process, preferably through a small hole in the container wall 18a (not shown) in a fully automatic process using a cannula and a dispensing unit. After the filling, the hole is closed, for example, it is melted shut, and the entire inhaler component is packed air-tight.

The liquid container 18 has at its lower end a slitlike supply opening 20 (see FIG. 5-6, FIG. 9-10). The second capillary gap segment 16b draws all liquid material 17 through this supply opening 20. The capillary coupling occurs by a shoulder 21 formed by the liquid container wall 18a. Thanks to the shoulder 21, one wall segment of the supply opening 20 is lengthened outwardly (see FIG. 9). The forces of adhesion acting on the lengthened wall segment have the effect of a small quantity of liquid material 17 escaping from the supply opening 20. The effect is enough for the liquid material 17 to also reach the circuit board 11, which abuts by its edge 11c against the shoulder 21 (see FIG. 6 and FIG. 9). In an alternative embodiment, the circuit board 11 rests by its back side 11b on the shoulder 21 (see FIG. 12). As soon as the liquid material 17 wets the back side 11b of the circuit board 11, the second capillary gap segment 16b can produce its suction action and take up liquid material 17. For stiffness, the shoulder 21 thrusts against the housing 3 by a web 22.

The slitlike supply opening 20 has a widening, roughly in the middle. The widening forms a ventilation opening 23. The ventilation opening 23 communicates with a ventilation groove 24, worked into the circuit board 11 on its back side 11b, which in turn communicates via the cavity 12 with an interior space under atmospheric pressure. The ventilation opening 23 and the ventilation groove 24 bring about a pressure equalization, in that each portion of liquid material 17 that is taken up by the second capillary gap segment 16b is immediately replaced by an equal-volume portion of air.

As is best shown by FIGS. 10 and 11, the first capillary gap segment 16a and the second capillary gap segment 16b are joined together by a third capillary gap segment 16c. The third capillary gap segment 16c is formed by the circuit board edge 11c and an adjacent housing wall 3a. The platelike top piece 14 that is connected to the circuit board is used for the exact placement of the third capillary gap segment 16c. This adjoins the housing wall 3a and projects beyond the edge of the circuit board 11c by a precisely defined measure. The measure corresponds to the gap width of the third capillary gap segment 16c and typically amounts to 0.3 mm. The circuit board 11 and the platelike top piece 14, which as already mentioned form a preassembled unit, must thus be joined precisely.

The three capillary gap segments 16a, 16b, 16c together form the capillary gap 16. The capillary gap 16 thus consists of an extended, interconnected capillary gap system, which partly encloses the circuit board 11. Leaving out of consideration the segments of the circuit board 11 protruding from the housing 3, i.e., the insert tongues 8a, then in the specific sample embodiment distinctly more than 50% of the circuit board surface form boundary walls of the capillary gap 16. The resulting beneficial effects with regard to the buffering of the liquid material 17, as well as the supply reliability and supply capacity, have already been discussed. A basic requirement for achieving these favorable effects is that the liquid material 17 sufficiently wet all exposed surfaces. To make sure of this, the affected parts—namely the liquid container 18a, the circuit board 11 and compound structures 10, the top piece 14 and at least parts of the housing 3—should undergo hydrophilic treatment in a suitable process even prior to assembly. Suitable processes are hydrophilic treatment in oxygen plasma and hydrophilic treatment by means of plasma polymerization. Both processes are offered, for example, by the firm Diener electronic GmbH u. Co. KG, www.plasma.de, on a subcontract order basis. Furthermore, this firm is able to design and erect suitable plants for mass production according to the client's specifications.

Before going further into the mode of operation of the inhaler according to the invention, we shall now describe additional parts of the inhaler component 2. Even though these parts might not be directly relevant to the invention, their description still contributes to a better understanding of the function of the invented inhaler component as a whole, and to further assure the implementation of the invention: between the top piece 14 and the housing 3 there are arranged two open-pore, absorbent sponges 25a, 25b (see FIG. 4g and FIG. 11). The space between the sponges forms, together with the recess 15, a chamber 26 (also see FIG. 8), in which the actual formation of the mixture of vapor and air and/or condensation aerosol occurs. The sponges 25a, 25b take up condensate deposits formed from the vapor phase into their pores and prevent freely movable condensate accumulations from forming in the inhaler component 2, which might impair the function of the inhaler component. Such condensate accumulations can also be a problem from a hygiene standpoint, especially if they get into the user's oral cavity through the mouth piece 4. The sponges 25a, 25b preferably consist of a fine-pore fiber compound structure. The firm Filtrona Fibertec GmbH, www.filtronafibertec.com, specializes in the manufacture of such fiber compound structures, processing both cellulose acetate fibers bound by means of triacetin and also thermally bound polyolefin and polyester fibers.

Figure 4G:
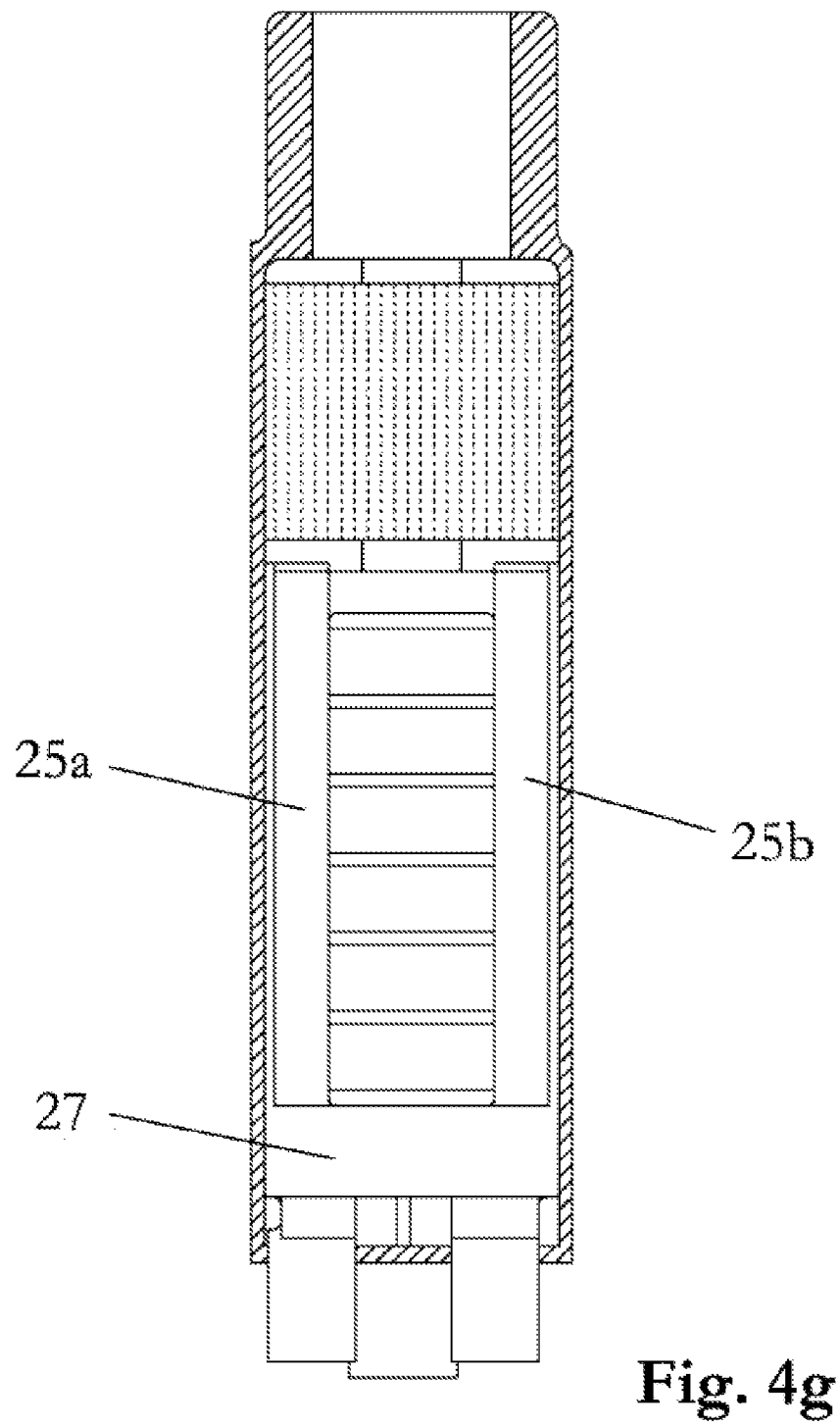

The sponges 25a, 25b are mounted on angle profiles 27a, 27b formed from a U-beam 27 (see FIG. 4g and FIG. 11). The beam 27 is joined to the top piece 14 by a glue connection. The beam 27 and angle profiles 27a, 27b preferably consist of a hydrophobic plastic. The hydrophobic material acts like a moisture barrier and ensures that no liquid material 17 can get to the sponges 25a, 25b by capillary effects. In the legs 27c joining the angle profiles 27a, 27b, at the side facing the top piece 14, there is made a depression 28 which, together with the top piece 14, forms an air nozzle 29 (see FIG. 9 and FIG. 10). The air nozzle 29, as shall be discussed more closely hereafter, serves to bring ambient air into the chamber 26. So that condensate deposits do not block the air nozzle 29, it is recommended to cover the surface of the top piece 14 with a thin hydrophobic adhesive tape (not shown) in the region of the air nozzle 29.

The supplying of the inhaler component 2 with ambient air to form the mixture of vapor and air and/or condensation aerosol occurs via a suction snorkel 30 formed by the housing 3 (see FIG. 3a/3b and FIG. 8). The suction snorkel 30 is arranged at the end of the inhaler component 2 opposite the mouth piece 4. This position best protects against entry of rain water. In the connected state, the suction snorkel 30 of the inhaler component 2 projects through a hole 31 formed by the main housing 5 of the inhaler part 1 (see FIG. 2). There is a flow throttle 32 in the suction snorkel 30. The flow throttle 32 has the purpose of creating flow resistance, similar to that of a cigarette, so that the user feels a similar draw resistance to that when drawing on a cigarette. Specifically, the flow resistance should be in the range of 8-16 mbar for a flow rate of 1.05 L/min and have the most linear characteristic possible. The flow throttle 32 is required when the resulting mixture of vapor and air and/or condensation aerosol is to be supplied as with a cigarette, namely, by drawing into the oral cavity (draw volume around 20-80 mL), possibly followed by an inhalation into the lungs. This mode of operation is recommended primarily when the liquid material 17 contains nicotine. The flow throttle 32 is not needed, however, when the inhaler is to provide a direct lung inhalation in a single step, as is the case with most medical inhalers. The flow throttle 32 consists preferably of a fiber compound structure similar to a cigarette filter, wherein the density of the material should be attuned to the aforementioned flow characteristic. The material, in turn, can be ordered from the firm Filtrona Fibertec GmbH, www.filtronafibertec.com.

In the following, the function of the inhaler shall be described in detail: a user attaches a new inhaler component 2 to the reusable inhaler part 1. The electrical circuit 7 registers the connection and may order to carrying out of certain preparatory operations, such as one or more evaporation cycles with the aim of supplying the compound structures 10 with fresh liquid material 17 and/or bringing about stationary conditions. Once these operations are concluded, the electrical circuit 7 signals the readiness of the inhaler, for example, through a light-emitting diode. The user brings up the mouth piece 4 of the inhaler to his mouth and activates the switch 7a. At the same time, he begins to draw on the mouth piece 4. The partial vacuum produced in this way has the effect that air flows from the surroundings into the suction snorkel 30. After the air has passed through the flow throttle 32, the flow bends at a right angle (see arrows in FIG. 8 and FIG. 9) and emerges into a plenum chamber 33, where the air accumulates and is then supplied uniformly to the slitlike air nozzle 29. The air flow is accelerated in the air nozzle 29 and enters with a high exit velocity into the chamber 26.

Activating the switch 7a has the effect of turning on the heating current circuit 7. The heating current is preferably switched by means of a power MOSFET, and the supplied power can be adapted to the particular requirements by a duty cycle. This adapting can also be done in certain limits by the user via an interface, making it possible for him to influence the resulting quantity of aerosol or smoke. The heating current is switched on for a predetermined period of time ("heating period"), typically amounting to 1.0-1.8 seconds. The heating current is taken to the compound structures 10 via the insert tongues 8a and the conductor tracks 13 of the circuit board 11 and brings about a lightning-fast heating of the compound structures 10 and the liquid material 17 stored in the wicks, whereupon the liquid material 17 evaporates. The vapor is emitted into the chamber 26, where it mixes with the air flowing in through the air nozzle 29. The arrangement and dimensioning of the air nozzle 29 produces a fast and uniform flow across the compound structures 10. This makes sure that the vapor released by the compound structures 10 encounters approximately the same mixture conditions everywhere, and the mixture of vapor and air is intimate. The air brings about a cooling of the vapor, so that a condensation aerosol can also form, provided the evaporated liquid material 17 contains substances with sufficiently low vapor pressure—so-called aerosol-forming substances. A typical example of such aerosol-forming substances is glycerol.

The mixture of vapor and air and/or condensation aerosol formed in the chamber 26 finally flows through yet another cooler 34 in the sample embodiment, before it is presented to the user for inhaling via the mouth piece 4 (see FIG. 4g and FIG. 8). The cooler 34 can consist, for example, of a porous filler material, a fleecelike fiber material, or an open-cell foam material whose pores are flowed through by the resulting mixture of vapor and air and/or condensation aerosol. The cooler 34 can also be multistaged, wherein the individual cooler stages have different properties. If the material being evaporated contains nicotine, it may be advantageous to coat the cooler material of at least one cooler stage with a suitable absorbent, such as citric acid. The absorbent extracts volatile nicotine fractions from the flowing condensation aerosol, which would otherwise be deposited in the oral cavity and throat, which is neither pharmacokinetically nor organoleptically desirable. Moreover, fragrances such as menthol can be added to the cooler material.

Suitable fleecelike fiber materials can be ordered, for example, from the firm Freudenberg Vliesstoffe KG, www.freudenberg-filter.com. The material consisting of polyolefin fibers and marketed under the name Viledon® filter mats is prepared by customer specification, and the material properties can be attuned so that the end product is largely permeable to the fine particles of the resulting condensation aerosol. A suitable foam material can be ordered, for example, from the firm Dunlop Equipment, www.dunlop-equipment.com. This supplier offers Ni and NiCr foam under the product name Retimet® (Grade 80) with a porosity of 90-95% and a pore diameter of around 300 µm in slabs up to thickness of 15 mm. According to an oral communication from firm representatives, even somewhat more fine-pored foams can be produced from a technological standpoint. The metal foams, furthermore, can be additionally compacted by roll treatment. The slabs can be further processed by laser cutting or wire erosion. Ni foam and especially NiCr foam are characterized by high strength, as well as high temperature and oxidation resistance. These properties make advisable a recycling and reusing of the relatively expensive metal foams at the end of the useful life of the inhaler component 2. If the liquid material 17 contains nicotine, the inhaler component 2 should be provided to the consumer only in return for a suitable deposit. This makes sure that the majority of the coolers 34, sponges 25a, 25b and liquid containers 18 contaminated with nicotine residue will be properly disposed of and possibly recycled.

At the end of the heating period, the circuit 7 deactivates the switch 7a for a couple of seconds. The deactivation is reported to the user, for example, by a light-emitting diode, and is necessary so that the compound structures 10 can cool down, and the wicks can again take up new liquid material 17. The liquid transport is brought about by the capillarity of the compound structures 10 and their wicks. The wicks take up the liquid material 17 through the compound structure end segments 10a, 10b from the first capillary gap segment 16a (see FIG. 4b/4f and FIG. 11). Thus, the wicks are infiltrated from two sides. The uptake of liquid material 17 from the first capillary gap segment 16a induces a capillary pressure in the capillary gap 16 that works its way back to the liquid container 18. The capillary pressure has the consequence that liquid material 17 flows from the liquid container 18 across the slitlike supply opening 20 into the second capillary gap segment 16b (see arrows in FIG. 4a). From there, the liquid material 17 goes through the third capillary gap segment 16c into the first capillary gap segment 16a, where it finally replaces the quantity of liquid removed. If, for whatever reason, disturbances in the capillary flow occur at one or more places in the capillary gap system 16, in most instances an alternative pathway will be found to get around the affected sites.

The quantity of liquid material 17 removed from the liquid container 18 is replaced by an equivalent quantity of air in the course of a pressure equalization. The pressure equalization occurs via the ventilation groove 24 and the ventilation opening 23. Once the compound structures 10 and wicks have again been fully infiltrated with the liquid material 17, the inhaler is ready for another evaporation cycle.

In an inverted position of use of the inhaler component 2—the mouth piece 4 points downward—the capillary coupling between the capillary gap 16 and the liquid material 17 in the liquid container 18 is lost, because the air cushion 35 always present in the liquid container 18 always points upwards in every position on account of buoyancy, i.e., in the inverted position of use it will come to lie in the region of the supply opening 20. An operation of the inhaler is still possible, at least for a certain number of draws or inhalations, because enough liquid material 17 has been buffered in the extended capillary gap system 16. Only when all capillary gap segments 16a, 16b, 16c are completely empty are the wicks liable to dry out. It is necessary, at latest at this time, to turn the inhaler component 2 back to a normal position of use, so that the capillary gap 16 can again fill with the liquid material 17, which process incidentally takes only a few seconds.

In conclusion, there shall be further disclosed, as an example, a nicotine-containing preparation of the liquid material 17, which has been evaporated in prototypes (see table 1). The condensation aerosol formed and given off in this case came very close to the smoke of a conventional cigarette in terms of pharmacological, pharmacokinetic and organoleptic effects. All of the listed ingredients are also found in cigarette smoke.

TABLE 1

| Substance | CAS number | Wt. % |
| --- | --- | --- |
| Water | 7732-18-5 | 52.88 |
| Ethanol | 64-17-5 | 4.14 |
| glycerol (E422) | 56-81-5 | 40.04 |
| Nicotine | 54-11-5 | 1.33 |
| lactic acid (E270) | 50-21-5 | 0.33 |
| succinic acid (E363) | 110-15-6 | 0.33 |
| benzoic acid (E210) | 65-85-0 | 0.24 |
| acetic acid (E260) | 64-19-7 | 0.71 |
| | Total: | 100.00 |

It should also be pointed out that the invention of course is not limited to one or several sheetlike compound structures 10 according to the sample embodiment just described. Alternatively, the compound structures can also be linear or threadlike. Moreover, the compound structures can be electrically interconnected in any way desired. Finally, the invention also includes devices in which the liquid container 18 can be separated from the housing 3, so that the liquid container 18 can be replaced by a new liquid container as soon as it is empty.

LIST OF REFERENCE NUMBERS 1 reusable inhaler part
2 interchangeable inhaler component
3 housing
3a housing wall
4 mouthpiece
5 main housing
6 battery
7 electrical circuit
7a switch
8a insert tongues
8b insert sockets
9a guide lugs
9b guide grooves
10 sheetlike compound structures
10a, 10b compound structure end segments
11 carrier plate, circuit board, multilayer circuit board
11a circuit board front side
11b circuit board back side
11c circuit board edge
12 cavity
13 conductor tracks
14 top piece
15 recess
16 capillary gap, capillary gap system
16a first capillary gap segment
16b second capillary gap segment
16c third capillary gap segment
17 liquid material
18 liquid container
18a liquid container wall
19 spacer
20 supply opening
21 shoulder
22 web
23 ventilation opening
24 ventilation groove
25a, 25b open-pore, absorbent sponges
26 chamber
27 U-beam
27a, 27b angle profiles
27c leg
28 depression
29 air nozzle
30 suction snorkel
31 hole
32 flow throttle
33 plenum chamber
34 cooler
35 air cushion

The invention claimed is:

1. An inhaler component for the formation of a vapor and air mixture and/or a condensation aerosol by evaporation of a liquid material, comprising:
   a housing;
   an electrical heating element configured to evaporate a portion of a liquid material;
   a wick with a capillary structure, the wick forming a compound structure with the heating element and configured to automatically supply the heating element with the liquid material;

a carrier plate carrying the compound structure and to which the heating element makes electrical contact; and a capillary gap at least partly formed by the carrier plate, and configured to automatically supply the compound structure with the liquid material via an end segment of the wick that protrudes into the capillary gap, the front side of the carrier plate and the back side of the carrier plate forming boundary walls for at least a portion of the capillary gap.

2. The inhaler component according to claim 1, wherein an edge of the carrier plate also forms at least a portion of a boundary wall of the capillary gap.

3. The inhaler component according to claim 2, wherein the capillary gap at least partly encloses the carrier plate.

4. The inhaler component according to claim 1, wherein over 50 percent of the carrier plate surface form boundary walls of the capillary gap.

5. The inhaler component according to claim 1, wherein the capillary gap is formed at least partially by the carrier plate and an adjoining wall of the housing.

6. The inhaler component according to claim 1, further comprising a liquid container containing the liquid material from which the capillary gap draws the liquid material, wherein the capillary gap is at least partially formed by the carrier plate and an adjacent wall of the liquid container.

7. The inhaler component according to claim 6, wherein the capillary gap communicates, via a supply opening in the wall of the liquid container, with the liquid material in the liquid container, the wall of the liquid container forming a shoulder at the edge of the supply opening and the carrier plate abutting against the shoulder with its edge.

8. The inhaler component according to claim 6, wherein the capillary gap communicates, via a supply opening in the wall of the liquid container, with the liquid material in the liquid container, the wall of the liquid container forming a shoulder at the edge of the supply opening and the carrier plate abutting against the shoulder with one of the front side and the back side.

9. The inhaler component according to claim 1, wherein the carrier plate comprises a circuit board.

10. An inhaler, comprising an inhaler component including:

a housing;

an electrical heating element configured to evaporate a portion of a liquid material;

a wick with a capillary structure, the wick forming a compound structure with the heating element and configured to automatically supply the heating element with the liquid material;

a carrier plate, the compound structure disposed on the carrier plate, the carrier plate configured to make electrical contact with the heating element; and a capillary gap at least partly defined by the carrier plate, and configured to automatically supply the compound structure with the liquid material via an end segment of the wick that protrudes into the capillary gap, the capillary gap at least partially defined by boundary walls including the front side of the carrier plate and the back side of the carrier plate.

11. The inhaler according to claim 10, wherein an edge of the carrier plate also defines at least a portion of a boundary wall of the capillary gap.

12. The inhaler according to claim 11, wherein the capillary gap at least partly encloses the carrier plate.

13. The inhaler according to claim 10, wherein over 50 percent of the carrier plate surface defines the boundary walls of the capillary gap.

14. The inhaler according to claim 10, wherein the capillary gap is defined at least partially by an adjoining wall of the housing.

15. The inhaler according to claim 10, further comprising a liquid container containing the liquid material from which the capillary gap draws the liquid material, wherein the capillary gap is at least partially defined by an adjacent wall of the liquid container.

16. The inhaler according to claim 15, wherein the capillary gap is configured to communicate, via a supply opening in the wall of the liquid container, with the liquid material in the liquid container, the wall of the liquid container defining a shoulder at the edge of the supply opening and the carrier plate abutting against the shoulder with its edge.

17. The inhaler according to claim 15, wherein the capillary gap is configured to communicate, via a supply opening in the wall of the liquid container, with the liquid material in the liquid container, the wall of the liquid container defining a shoulder at the edge of the supply opening and the carrier plate abutting against the shoulder with one of the front side and the back side.

18. The inhaler according to claim 10, wherein the carrier plate comprises a circuit board.

* * * * *